(12) United States Patent
Chae et al.

(10) Patent No.: US 10,076,572 B2
(45) Date of Patent: Sep. 18, 2018

(54) **PHOTODYNAMIC THERAPY FOR TREATING *CLOSTRIDIUM DIFFICILE* INFECTION USING CHITOSAN AND TETRACYCLINE**

(71) Applicant: CATHOLIC UNIVERSITY INDUSTRY ACADEMIC COOPERATION FOUNDATION, Seoul (KR)

(72) Inventors: Hiun Suk Chae, Seoul (KR); Sung Sook Choi, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 650 days.

(21) Appl. No.: 14/690,293

(22) Filed: Apr. 17, 2015

(65) Prior Publication Data
US 2016/0303237 A1    Oct. 20, 2016

(51) Int. Cl.
*A61K 41/00*  (2006.01)
*A61N 5/06*  (2006.01)
*A61K 31/65*  (2006.01)
*A61K 31/722*  (2006.01)

(52) U.S. Cl.
CPC .......... *A61K 41/0057* (2013.01); *A61K 31/65* (2013.01); *A61K 31/722* (2013.01); *A61N 5/062* (2013.01); *A61N 5/0624* (2013.01); *A61N 2005/0661* (2013.01)

(58) Field of Classification Search
None
See application file for complete search history.

(56) References Cited

U.S. PATENT DOCUMENTS

2009/0304803 A1* 12/2009 Hasan ................ A61K 41/0071
                                                              424/497
2010/0129432 A1*  5/2010 Chen ....................... A01N 25/00
                                                              424/450

OTHER PUBLICATIONS

Bornstein et al. (Photochemistry and Photobiology 2010 86:617-627 (Year: 2010).*
Rineh et al. (Expert Reviews in Anti-Infective Therapy 2014 12(1):131-150 (Year: 2014).*
Martin et al. (Journal of Bacteriology 1987 169(6):2516-2522 (Year: 1987).*
Kim et al, "Photodynamic Bactericidal Activity (in vitro) using Tetracycline and Chitosan against Clostridium dfficile", Intestinal Research, Apr. 19, 2014, Department of Internal Medicine, Uijongbu St. Mary's Hospital, Catholic University of Medical College—3 pages.

* cited by examiner

*Primary Examiner* — Robert A Wax
*Assistant Examiner* — Caralynne E Helm
(74) *Attorney, Agent, or Firm* — Knobbe Martens

(57) ABSTRACT

Effective Photodynamic therapy (PDT) against *C. difficile* is provided using a composition including chitosan and tetracycline.

8 Claims, 3 Drawing Sheets
(1 of 3 Drawing Sheet(s) Filed in Color)

PHOTODYNAMIC THERAPY FOR TREATING *CLOSTRIDIUM DIFFICILE* INFECTION USING CHITOSAN AND TETRACYCLINE

FIELD

The disclosure relates to photodynamic bactericidal activity.

BACKGROUND

*Clostridium difficile* (*C. difficile*) is an anaerobic gram positive, spore forming bacteria that causes intestinal disease varying from s mild diarrheal illness to severe colitis like pseudomembranous colitis. *C. difficile* produce enterotoxin and cytotoxin to develop various intestinal diseases.

*C. difficile* infection (CDI) is an inflammation of the colon characterized by diarrhea and pseudomembranous colitis showing the appearance of distinct plaques and neutrophil accumulation in the intestinal lumen. The risk factors for CDI are old age, hospitalization and use of broad spectrum antimicrobial agents. Exposure to bactericidal agents leads to disturbance of the normal gut flora environment, allowing *C. difficile* to proliferate and reach high densities in the colon which may lead to CDI. Most causative antibiotics are cefotaxims, amoxicillin, penicillin, quinolone and aminoglycoside.

SUMMARY

One aspect of the present invention provides a composition comprising chitosan as a boostering agent in combination with photo sensitizer to enhance bactericidal activity against *C. difficile*.

Another aspect of the present invention provides A photodynamic bactericidal composition comprising chitosan and tetracyclin as effective component.

Yet another objective of the present invention provides a method for enhancing bactericidal activity against *Clostridium difficile* comprising: a) treating *Clostridium difficile* with tetracycline and chitosan; and b) irradiating the *Clostridium difficile* treated with the tetracycline and chitosan The details of embodiments of the invention are set forth in the accompanying detailed description below. Although any materials similar to those described herein can be used in the practice or testing of the present invention, illustrative examples are now described. Other embodiments, aspects and features of the present invention are either further described in or will be apparent from the ensuing description, examples and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF EMBODIMENTS

Figure 1:
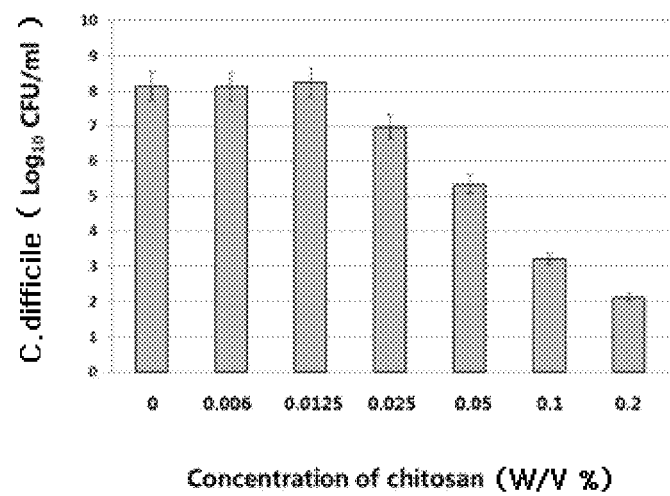
FIG. 1 shows a graph of a bactericidal activity of chitosan itself against *C. difficile*.

Here, the term "a," "an", and "the" include both singular and plural references unless the context clearly dictates otherwise. At times, the claims and disclosure may include terms such as "one or more" or "at least one", however, the absence of such terms is not intended to mean, and should not be interpreted to mean, that a plurality is not conceived for a particular embodiment.

As used herein, the term "comprising" or "comprises" is intended to mean that the composition include the recited component, and may additionally include any other components.

To treat CDI, the most common drug of choice includes metronidazole and vancomycin. Metronidazole is used to mild and moderate CDI, but the number of treatment failure with this antibiotic is increasing. Vancomycin causes few side effects, but it has reluctance of use for high cost and the increase of resistant strains. Increasing failure, antibiotic resistant and recurrence rate has led to find out other antibiotics or other methodology for the treatment of CDI.

Rifaximin, tigecyclin and fidaxomicin are now tried for the treatment of CDI. Other therapeutic methods for the treatment of CDI except antibiotics are fecal transplantation, probiotics and photodynamic therapy. Fecal transplantation looks promising for treatment of gut microbial infections, but there are some challenges that need to be addressed in further studies. For the treatment of CDI, probiotics are prescribed with antibiotics but the composition of the gut bacteria is only changed temporarily and reverts back to steady state when probiotics are stopped.

Photodynamic therapy (PDT) is a method using a photosensitizer (PS) and light sources of a specific wavelength for treatment of malignant tumors or localized infectious diseases. Reactive oxygen species generated by the photodynamic reaction induce damage to multiple cellular structures including the cell membrane, cell wall and nucleic acids, which leads to bactericidal and anticancer effects.

According to our previous research, chitosan showed effective synergistic bactericidal activity (Synergistic in vitro photodynamic bactericidal activity of methylene blue and chitosan against *Helicobacter pylori* 26695. 11(2014) 526-532, S. S. Choi, H. K. Lee and H. S. Chae). In this study, we also applied chitosan to increase the bactericidal effect during PDT and to decrease the concentration of tetracycline and to reduce the harmful effect of tetracycline's phototoxicity against human cells and tissues.

The term "photosensitizer" refers to a chemical compound that absorbs electromagnetic radiation, most commonly in the visible spectrum although not limited thereto, and releases the energy in another form, most commonly as reactive oxygen species and/or as thermal energy. The Reactive oxygen species generated by the photodynamic reaction induce damage to multiple cellular structures including the cell membrane, cell wall and nucleic acids, which leads to bactericidal and anticancer effects. The chemical compound is not particularly limited, and examples are methylene blue, toluidine blue O, and protoporphyrin IX.

Embodiments of the present invention are directed to a composition comprising chitosan as a boostering agent in combination with tetracycline (TC) to enhance bactericidal activity against *Clostridium difficile* and a method for eradicating *Clostridium difficile* comprising: applying to an area of *Clostridium difficile* infection tetracycline and chitosan; and treating the infected area with the photodynamic therapy.

*Clostridium difficile* is an anaerobic toxigenic bacterium, and causes a severe colitis with high recurrence and severe morbidity.

*Clostridium difficile* infection (CDI) is worldwide disease and mainly caused by *C. difficile*. The use of antibiotics in hospitalized patients leads to depletion of normal flora and offers chance to colonize opportunistic pathogens such as *C. difficile*. Antibiotic therapy to treat CDI is not the best way to eradicate *C. difficile* because of failure and recurrence. It is therefore necessary to develop other non-antibiotic eradication methods.

Antibiotics and other therapeutic methods, fecal transplantation, probiotics and photodynamic therapy, are now trying for CDI.

PDT is one of the other therapeutic alternatives and there have been few studies about PDT worldwide due to poorly effective photosensitizer to *C. difficile* and other few ancillary method to enhance PDT. Also, phototoxicity caused by photosensitizer is reported when using UVA; sunburn, edema, and red spots. Thus, the alternative one to maximize photodynamic effect and to reduce dosage of photosensitizer, has been needed.

Compositions according to embodiments of the present invention enhance bactericidal activity against *C. difficile* or decrease the concentration of photosensitizer. Thus, compositions comprising chitosan is administered simultaneously, separately, or sequentially with the tetracyclin.

In one embodiment, the applicant has found that cells were not affected with concentrations of chitosan as high as 0.0125 w/v % for 30 min to exclude any inhibitory activity of chitosan itself.

In another embodiment, the applicant has found that cells were not affected by incubation with tetracycline as high as 1 mg/mL for 30 min to exclude any inhibitory activity of tetracycline itself.

In yet another embodiment, the applicant has found synergistic photodynamic bactericidal activity of chitosan in combination with tetracycline and that a composition comprising chitosan is useful to enhance bactericidal activity against *Clostridium difficile*.

Embodiments of the present invention will be described in detail below with reference to the accompanying drawings. While the present invention is shown and described in connection with embodiments thereof, it will be apparent to those skilled in the art that various modifications can be made without departing from the spirit and scope of the invention.

In embodiments, *Clostridium difficile* infection is treated using a method of photodynamic therapy using chitosan and tetracycline. The method includes applying chitosan to an area of the *Clostridium difficile* infection, applying tetracycline to the area, and applying light beams to the area subsequent to or while applying the chitosan and tetracycline.

In some embodiments, chitosan and tetracycline are applied to the infected area separately or together. In some embodiments, chitosan and tetracycline are applied to the infected area together as part of a composition. In embodiments, the composition includes chitosan at a concentration in the range of 0.006 w/v %-0.0125 w/v %. In embodiments, the composition comprises tetracycline at a concentration in the range of 0.05 mg/ml 0125 w/v %. In embodiments, the tetracycline is applied at a concentration of 0.05, 0.06, 0.07, 0.08, 0.09, 0.1, 0.12, 0.14, 0.16, 0.18, 0.2, 0.25, 0.3, 0.35, 0.4, 0.45, 0.5, 0.55, 0.6, 0.65, 0.7, 0.75, 0.8, 0.85, 0.9, 0.95, 1 mg/ml. In embodiments, the tetracycline is applied to the infected area at a concentration in a range formed by any two numbers listed in the immediately preceding sentence. In embodiments, the composition includes the chitosan at a concentration in the range of 0.006 w/v %-0.0125 w/v % and the tetracycline at a concentration in the range of 0.1 mg/ml tosan at a In embodiments, the light beams applied to the infected area includes ultraviolet A (UVA) light beams. The light beams are applied to the infected area for 2, 3, 4, 5, 6, 7, 8, 9, 10, 12, 14, 16, 18, 20, 22, 24, 26, 28, 30, 32, 34, 36, 38, 40, 45, 50, 55, 60 minutes. In embodiments, the light beams are applied to the infected area for a period defined by any two numbers listed in the immediately preceding sentence.

EXAMPLES

1. Bacterial Strain and Culture Media

The standard strain of *Clostridium difficile* was provided by Korean Collection for Type Cultures (*C. difficile*, KCTC 5009). *C. difficile* was cultured at 37° C. in a standard anaerobic condition on Clostridia reinforced agar (Oxoid, Cambridge, CB5 8BZ, UK).

2. Chemicals and Instruments

Tetracycline, chitosan (low molecular weight), and ethidium bromide monoazide (EMA) were purchased from Sigma (Sigma Chemical Co., St. Louis, Mo.). A stock solution of tetracycline was prepared in water at a concentration of 10 mg/mL and stored for a maximum of 2 weeks at 4° C. in the dark before use. A stock solution of chitosan (1% w/v) was prepared in 1% acetic acid and used within one month. The light source for UVA was lamp (315-400 nm) for treatment of psoriasis (UV801KL, Waldmann Medical division, Germany). The irradiation procedure was performed in a dark and closed box and *C. difficile* containing plates were placed at a distance of 10 cm from the light source.

Example 1. Inhibitory Activity of Chitosan Itself

The stock solution of chitosan (1% w/v) was diluted with phosphate-buffered saline (PBS) to prepare media containing various concentrations of chitosan. Following incubation of *C. difficile* in various concentration of chitosan (0 w/v % to 0.2 w/v %) for 30 min, cells were washed with fresh PBS and then serially diluted tenfold with PBS. Colonies that formed after 2 days of incubation at 37° C. were counted.

The bactericidal activity of chitosan against *C. difficile* was determined to exclude any inhibitory activity of chitosan itself. As shown in FIG. 1, cells were not affected by incubation with concentrations of chitosan as high as 0.0125 w/v % for 30 min.

Example 2. Inhibitory Activity of Tetracycline Itself

To test inhibitory activity of tetracycline itself against *C. difficile* during PDT, *C. difficile* was incubated with various concentration of tetracycline (0.05 mg/mL to 2 mg/mL) for 30 min. After incubation, cells were washed with fresh PBS and then serially diluted tenfold with PBS. Colonies that formed after 2 days of incubation at 37° C. were counted.

Figure 2:
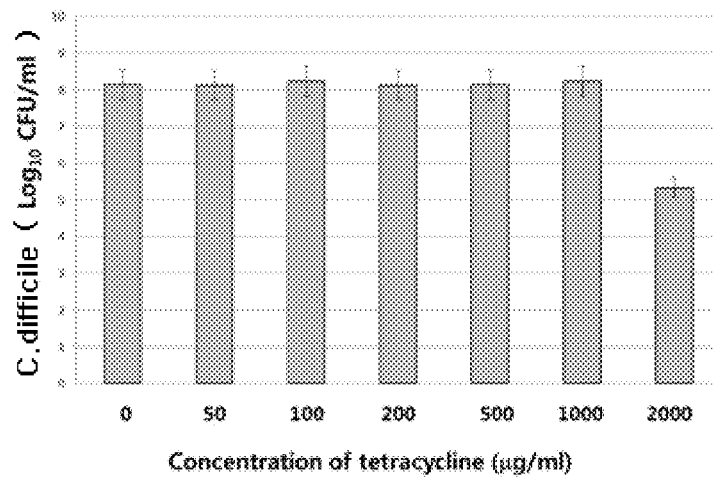
FIG. 2 shows a graph of a bactericidal activity of tetracycline itself against *C. difficile*.

The bactericidal activity of tetracycline itself against *C. difficile* was determined to exclude any inhibitory activity of tetracycline itself. As shown in FIG. 2, cells were not affected by incubation with tetracycline as high as 1 mg/mL for 30 min.

Example 3. Synergistic Inhibitory Photodynamic Activity of Chitosan and Tetracycline Based on a modification of the method of Tegos (G. P. Tegos, M. R. Hamblin. Phenothiazinium bactericidal photosensitizers are substrates of bacterial multidrug resistance pumps. Antimicrob. Agents Chemother. 50 (2006)196-203.), *C. difficile* that had been stored at −70° C. was cultured in Clostridial agar medium for 3 days.

After successive subcultures for two days, the cells were collected and suspended in PBS at a concentration of 108 cells/mL. The cell suspension was exposed to tetracycline alone at concentrations of 0.05 mg/mL, 0.1 mg/mL, 0.5 mg/mL and 1 mg/mL, or to 0.0125% chitosan containing TC at a concentration of 0.05 mg/mL, 0.1 mg/mL, 0.5 mg/mL and 1 mg/mL for 30 min.

After samples were washed twice with PBS, the bacterial cell suspension was dispensed at a volume of 1000 µL in a plate for irradiation for 5, 10, 20 and 30 min. After irradiation, cells were serially diluted tenfold in PBS to give dilutions of $10^{-1}$ to $10^{-8}$ of the original concentrations, and a 10 µL aliquot of each dilution was spotted on a Clostridial agar plate. After 2 days incubation, the colonies were counted to obtain the number of colony-forming units. *C. difficile* without treatment with TC, chitosan and light served as the control.

Figure 3:
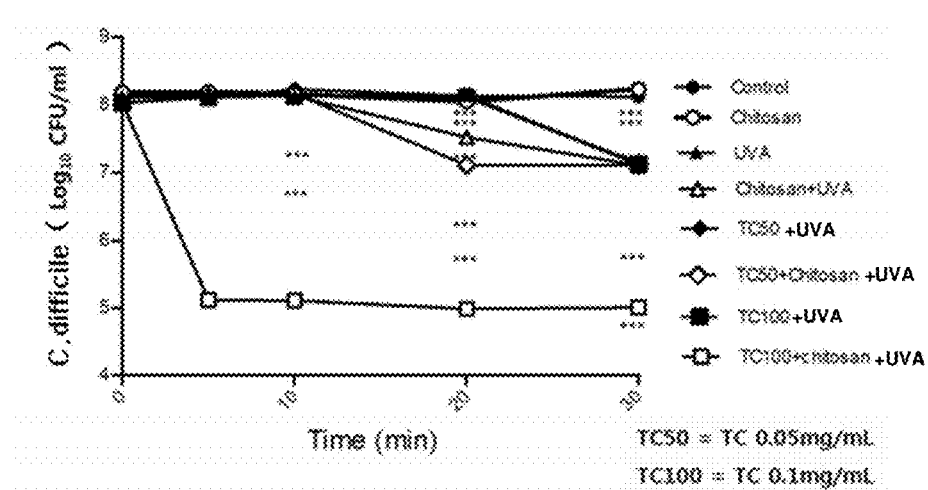
FIGS. 3 and 4 show graphs of a Synergistic bactericidal photodynamic activity of chitosan and tetracycline against *C. difficile*.
Figure 4:
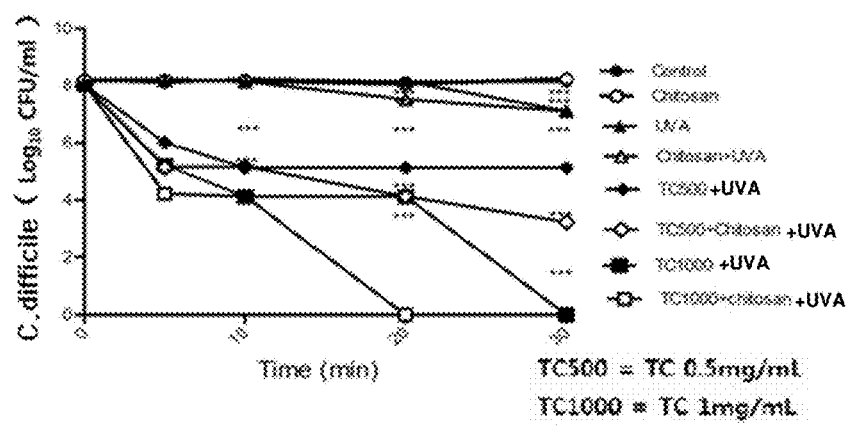
Figure 5:
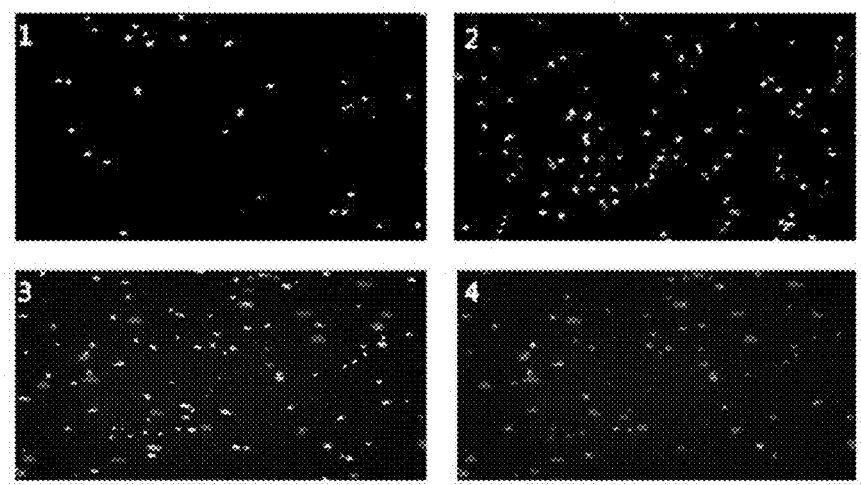
FIG. 5 depicts the membrane integrity of *C. difficile* after PDT by confocal microscopy using membrane-permeant and membrane-impermeant fluorescent DNA probe.

The bactericidal effect of PDT increased in proportion to both tetracycline concentration and duration of exposure to light, as shown in FIG. 3 and table 1 (low concentration of TC) and FIG. 4 and table 2 (high concentration of TC). The concentration of chitosan, 0.0125%, was chosen to exclude any bactericidal effect of chitosan itself. The number of viable cells in the control and chitosan treatment for 30 min showed almost no change over the elapsed time.

The groups treated with UVA, UVA+chitosan, TC 0.05 mg/mL+UVA and TC 0.1 mg/mL+UVA, viable cells were only decreased 10 times after 30 min irradiation ($1.2\times10^7$, $1.3\times10^7$, $1.12\times10^7$, $1.14\times10^7$ respectively). The group treated with TC 0.05 mg/mL+UVA+chitosan, 10 times of viable cells were decreased after 20 min irradiation. The group that treated with TC 0.1 mg/mL+UVA+chotsan, 1,000 time cells were decreased after 5 min irradiation ($1.23\times10^5$), but any more bactericidal effect was observed during the PDT.

In case of high concentration of TC, PDT with TC+chitosan showed potent bactericidal effect. The group treated with TC 0.5 mg/mL+UVA, viable cells were $1.10\times10^6$, $1.12\times10^5$, $1.11\times10^5$ and $1.13\times10^5$ after 5, 10, 20 and 30 min irradiation. The groups treated with TC 0.5 mg/mL+UVA+chitosan, viable cells were $1.12\times10^5$, $1.15\times10^5$, $1.12\times10^4$ and $1.23\times10^3$ after 5, 10, 20 and 30 min irradiation. The group treated with TC 1.0 mg/mL+UVA, viable cells were $1.21\times10^5$, $1.11\times10^4$, $1.13\times10^4$ and 0 after 5, 10, 20 and 30 min irradiation. The group treated with TC 1.0 mg/mL+UVA+chitosan, viable cells were $1.21\times10^4$, $1.12\times10^4$, 0 and 0 after 5, 10, 20 and 30 min irradiation.

TABLE 1

| | $Log_{10}$ CFU/mL (mean ± SD, n = 3) | | | | | | | |
|---|---|---|---|---|---|---|---|---|
| | | | | | 0.05 mg/mL TC | | 0.1 mg/mL TC | |
| Time (min) | control | chitosan | UVA | UVA + chitosan | UVA | UVA + chitosan | UVA | UVA chitosan |
| 0 | 8.20 ± 0.22 | 8.18 ± 0.26 | 8.13 ± 0.10 | 8.14 ± 0.87 | 8.11 ± 0.48 | 8.15 ± 0.36 | 8.03 ± 0.39 | 8.03 ± 0.12 |
| 5 | 8.09 ± 0.14 | 8.19 ± 0.36 | 8.18 ± 0.21 | 8.17 ± 0.59 | 8.11 ± 0.78 | 8.15 ± 0.25 | 8.11 ± 0.11 | 5.12 ± 0.21 |
| 10 | 8.23 ± 0.24 | 8.16 ± 0.18 | 8.15 ± 0.33 | 8.13 ± 0.67 | 8.13 ± 0.40 | 8.17 ± 0.57 | 8.13 ± 0.53 | 5.11 ± 0.0.22 |
| 20 | 8.13 ± 0.34 | 8.05 ± 0.33 | 8.14 ± 0.80 | 7.52 ± 0.36 | 8.11 ± 0.67 | 7.11 ± 0.28 | 8.11 ± 0.21 | 4.99 ± 0.29 |
| 30 | 8.12 ± 0.19 | 8.23 ± 0.29 | 7.12 ± 1.01 | 7.11 ± 0.62 | 7.14 ± 0.33 | 7.11 ± 0.12 | 7.12 ± 0.38 | 5.01 ± 0.35 |

TABLE 2

| | $Log_{10}$ CFU/mL (mean ± SD, n = 3) | | | | | | | |
|---|---|---|---|---|---|---|---|---|
| | | | | | 0.5 mg/mL TC | | 1 mg/mL TC | |
| Time (min) | control | chitosan | UVA | UVA + chitosan | UVA | UVA chitosan | UVA | UVA chitosan |
| 0 | 8.20 ± .22 | 8.18 ± 0.26 | 8.13 ± 0.10 | 8.14 ± 0.08 | 8.03 ± 0.48 | 8.03 ± 0.36 | 8.03 ± 0.39 | 8.03 ± 0.42 |
| 5 | 8.09 ± 0.14 | 8.19 ± 0.36 | 8.18 ± 0.21 | 8.17 ± 0.59 | 6.02 ± 0.76 | 5.13 ± 0.25 | 5.21 ± 0.11 | 4.21 ± 0.21 |
| 10 | 8.23 ± 0.24 | 8.16 ± 0.18 | 8.15 ± 0.33 | 8.13 ± 0.67 | 5.12 ± 0.10 | 5.15 ± 0.17 | 4.11 ± 0.23 | 4.12 ± 0.22 |
| 20 | 8.13 ± 0.34 | 8.05 ± 0.33 | 8.14 ± 0.80 | 7.52 ± 0.36 | 5.11 ± 0.27 | 4.12 ± 0.18 | 4.11 ± 0.21 | 0 |
| 30 | 8.12 0.19 | 8.23 ± 0.29 | 7.12 ± 1.01 | 7.11 ± 0.62 | 5.11 ± 0.23 | 3.23 ± 0.12 | 0 | 0 |

Example 4. EMA-qPCR Analysis of *C. Difficile* DNA to Evaluate Cell Death and DNA Damage To evaluate the degree of compromise of the cell wall and membrane in the irradiated cells, quantitative real-time polymerase chain reaction (qPCR) was performed after the treatment of cells with ethidium bromide monoazide (EMA). EMA is a DNA-intercalating agent that can selectively enter those cells that have a compromised cell wall and membrane. Within these cells, it covalently links to DNA, and the EMA-linked DNA cannot be amplified by PCR. The use of EMA treatment and PCR can distinguish more disrupted cells. The 16S rRNA gene (a housekeeping gene of *C. difficile*) was selected as the target gene.

After treatment of cells with 0.5 mg/mL TC alone or TC+chitosan, and UVA irradiation for 30 min, each cell suspension was treated with 100 µg/mL of EMA. The samples were incubated in the dark for 5 min and subsequently exposed to light from a 650 W halogen lamp 20 cm above the tube for 1 min. The tubes were placed on ice prior to light exposure to minimize elevation of the temperature in the samples. DNA was extracted with the GeneAll Cell SV system (GeneAll, Seoul, Korea) according to the manufacturer's instructions. The target gene was a housekeeping gene (16S rRNA), and the primers to amplify 16S rRNA were as follows: (F) 5'-GTC CTC AAG GAA GAT AAT GAC GG-3', (R) 5'-TTC ACT CCT GAC TTG AAA GAC CG-3'.

The real-time PCR procedure for 16S rRNA was as follows: the reaction mixture was composed of 2 μL of DNA template mixed with 10 μL of Power SYBR Green PCR Master Mix (Life Technologies Pty Ltd, NY, USA), 0.5 μL of each primer and in a final volume of 20 μL. Step-One Plus Real-Time PCR System (Life Technologies Pty Ltd, NY, USA) was used with the following reaction conditions: 95° C. for 10 min, 40 cycles of 95° C. for 15 sec and 60° C. for 60 sec as the thermal cycling stage. The program for analytical melting was 15 sec at 95° C. and 60 sec at 60° C., and an increase to 95° C. at a ramp rate of 0.3° C. per second.

As shown in Table 3, the Ct values of EMA-qPCR were 12.030±0.020, 14.073±0.041, 19.629±0.075, 23.026±0.101 and 23.717±0.081 in control, UVA only, UVA+chitosan treatment, TC+UVA, TC+UVA+chitosan treatment, respectively.

This result shows that chitosan in combination with tetracycline boost damaging cell membrane and cell wall to enhance photodynamic activity.

TABLE 3

| DNA samples | Ct value |
|---|---|
| Control[a] | 12.02984 ± 0.020 |
| UVA[b] | 14.07315 ± 0.041 |
| UVA + Chitosan[c] | 19.62889 ± 0.075 |
| UVA + TC[d] | 23.02573 ± 0.101 |
| UVA + TC + chitosan[e] | 23.71733 ± 0.081 |

[a]Cells were incubated in anaerobic condition for 30 min without light, TC and chitosan
[b]Cells were incubated under only UVA irradiation
[c]Cells were incubated under UVA + chitosan (0.0125 w/v %)
[d]Cells were incubated under UVA + TC (0.5 mg/mL)
[d]Cells were incubated under UVA + TC (0.5 mg/mL) + chitosan (0.0125 w/v %)

Example 5. Evaluation of Membrane Integrity

The membrane integrity of *C. difficile* after PDT was evaluated by confocal microscopy using membrane-permeant and -impermeant fluorescent DNA probe (Live/Dead BacLight™ Bacterial Viability and Counting Kit; Molecular Probes Inc., Eugene, Oreg., USA). A compromised cell membrane was considered indicative of cell death.

The membrane-permeant DNA probe SYTO®9, when bound to DNA and excited at 488 nm, emits a green light (emission>505 nm). Propidium iodide, which is membrane impermeant, emits a red light (excitation, 543 nm; emission, >633 nm) when it binds to DNA, and quenches SYTO9 fluorescence. Therefore, viable bacteria will emit a green light but bacteria in which cell membrane integrity is compromised will fluoresce red.

After the irradiation experiment was performed as describe above, 1 ml of cells was centrifuged in a microcentrifuge at 10,000×g for 1-3 min to pellet them. After the supernatant was removed, half of the pellet was resuspended in 1 ml of 0.85% NaCl (for detection of live cell) and a second half of the pellet was resuspended in 1 ml 70% isopropyl alcohol (for the detection of dead cell). The samples were incubated at room temperature for 30-60 min with mixing every 15 min. After pelleting, the samples were washed with 0.85% NaCl and resuspended in 1 ml of 0.85% NaC.

977 ul of 0.85% NaCl was mixed with 1.5 ul of 3.34 mM SYTO9 nucleic acid stain, and added to 1.5 ul of 30 mM propidium iodide in a tube. A 10 μl aliquot of bacterial suspension was added and incubated for 15 min at room temperature, protected from light. After the cells were stained, their fluorescence was observed with confocal microscopy.

The membrane integrity of *C. difficile* after PDT was evaluated by confocal microscopy using membrane-permeant and-impermeant fluorescent DNA probe. In the control group, only green fluorescence was observed, indicating that cell membrane remained intact in the control group. In the group, which treated with UVA only or UVA plus TC at a concentration of 500 μg/ml, green fluorescence was still observed with red color. However, in the group which treated with UVA plus TC (0.5 mg/mL) plus chitosan (0.0125 w/v %), only red fluorescence was observed because most of the cells had ruptured. The synergistic bactericidal activity of TC and chitosan is more potent than TC only.

This result also shows that chitosan in combination with tetracycline boost damaging cell membrane and cell wall to enhance photodynamic activity.

Embodiments of the invention have been described above and modifications and alterations may occur to others upon the reading and understandings of this specification. The claims as follow are intended to include all modifications and alterations insofar as they come within the scope of the claims or the equivalent thereof.

What is claimed is:

1. A method of treating *Clostridium difficile* infection, the method comprising:
    applying chitosan to an area of the *Clostridium difficile* infection;
    applying tetracycline to the area; and
    applying light beams to the area subsequent to or while applying the chitosan and tetracycline,
    wherein each of chitosan and tetracycline is applied at a concentration that does not inhibit *Clostridium difficile* when applied alone, wherein the concentration of chitosan is in a range of 0.006 w/v % to 0.0125 w/v %, wherein the concentration of tetracycline is in a range of 0.05 mg/ml to 1 mg/ml.

2. The method of claim 1, wherein the light beams comprise ultraviolet (UV) light beams.

3. The method of claim 1, wherein the chitosan and tetracycline are applied together as part of a composition.

4. The method of claim 3, wherein the composition comprises the tetracycline at a concentration in the range of 0.1 mg/ml to 1 mg/ml.

5. The method of claim 3, wherein the light beams comprise ultraviolet A (UVA) light beams.

6. The method of claim 3, wherein the light beams are applied to the area for at least 5 minutes.

7. The method of claim 3, wherein the light beams are applied to the area for a period of 5 to 30 minutes.

8. The method of claim 3, wherein the light beams are applied to the area for a period of 5 to 20 minutes.

* * * * *